United States Patent [19]
Jew et al.

[11] Patent Number: 6,030,993
[45] Date of Patent: Feb. 29, 2000

[54] 2-HYDROXYPROPIONIC ACID DERIVATIVE AND ITS MANUFACTURING METHOD

[75] Inventors: Sang Sup Jew; Suk Ku Kang; Deuk Joon Kim, all of Seoul; Won Ki Kim; Hwa Jung Kim, both of Kyunggi-do; Chang Kiu Moon; Jeong Hill Park, both of Seoul; Young Ger Suh, Kyunggi-do; Bong Jin Lee, Seoul; Jee Woo Lee, Seoul; Ki Hwa Jung, Seoul; Moon Woo Chun, Seoul; Hoon Huh, Seoul; Eung Seok Lee, Seoul; Hyung Ook Kim, Seoul; Eun Kyung Kim, Daegu; Sung Jin Kim, Seoul; Jae Hoon Cheong, Kyunggi-do; Kwang Ho Ko; Bak Kwang Kim, both of Seoul, all of Rep. of Korea

[73] Assignees: Sang Sup JEW; Kwang Ho KO; Bak Kwang KIM, all of Seoul, Rep. of Korea

[21] Appl. No.: 09/214,388

[22] PCT Filed: Jul. 2, 1997

[86] PCT No.: PCT/KR97/00133

§ 371 Date: May 4, 1999

§ 102(e) Date: May 4, 1999

[87] PCT Pub. No.: WO98/00389

PCT Pub. Date: Jan. 8, 1998

[30] Foreign Application Priority Data

Jul. 2, 1996 [KR] Rep. of Korea ...................... 96-26777

[51] Int. Cl.$^7$ ........................ C07D 231/12; A61K 31/215

[52] U.S. Cl. ..................... 514/406; 514/438; 514/439; 514/461; 514/532; 549/66; 549/79; 549/501; 554/116; 560/11; 560/60; 560/61; 548/376.1

[58] Field of Search ................................ 554/116; 560/60, 560/11, 61; 514/532, 406, 461, 438, 439; 548/376.1; 549/66, 79, 501

[56] References Cited

U.S. PATENT DOCUMENTS 4,788,306  11/1988  Schieser et al. .

OTHER PUBLICATIONS

R. Huber et al., Abstract No. 16547of, "Pharmacokinetics of the new antidiabetic drug Etomoxir in man after administration of the unlabeled or carbon–14–labeled compound", Chemical Abstracts, vol. 110, No. 19, p. 13, col. 1, (1989).

W. Ho et al., Abstract No. 18266h, "Alkylglycidic acids: potential new hypoglycemic agents", Chemical Abstracts, vol. 106, No. 3, p. 578, col. 2, (1987).

*Primary Examiner*—Gary Geist
*Assistant Examiner*—Leigh C. Maier
*Attorney, Agent, or Firm*—Finnegan, Henderson, Farabow, Garrett & Dunner, L.L.P.

[57] ABSTRACT

This invention relates to a novel 2-hydroxypropionic acid derivative and its manufacturing method. Based on its mechanism to inhibit the CPT I, 2-hydroxypropionic acid derivative of this invention has blood glucose lowering effects so that the derivative may be effectively used as an antidiabetic agent having remarkable antidiabetic activity and fewer side effects.

8 Claims, No Drawings

2-HYDROXYPROPIONIC ACID DERIVATIVE AND ITS MANUFACTURING METHOD

This application is the national phase of PCT/RR97/00133, filed Jul. 2, 1997.

TECHNICAL FIELD

This invention relates to 2-hydroxypropionic acid derivative expressed by the following formula (1), its manufacturing method and antidiabetic agent containing it.

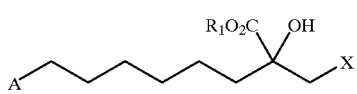

Wherein:

A is one selected from the radicals expressed by the following (i), (ii), (iii), (iv) and (v);

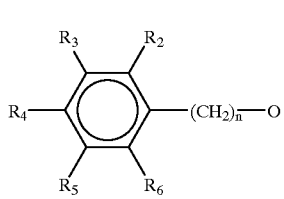

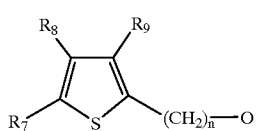

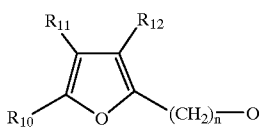

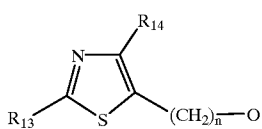

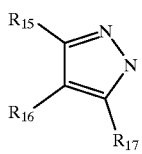

$R_1$ represents a lower alkyl;

X represents hydroxy, mesylate, tosylate or bromine.

(wherein $R_2$~$R_{17}$ represent independently hydrogen, halogen, alkoxy, lower alkyl, hydroxy, alkenyl, alkynyl, cyano or amino group; n denotes 0, 1 or 2).

BACKGROUND OF ART

The diabetic patients tend to suffer from some disorders such as inhibition of glucose uptake, inhibited glycolysis and increasing beta-oxidation of fatty acid in their peripheral tissues, which cause the use of fat for their body's energy source instead of glucose and lead to some diseases such as hyperglycemia, hyperlipidemia and hyperketonemia.

The beta-oxidation of fat in diabetic patients occurs in a mitochondrial substrate. Carnitine palmitoyl transferase I (CPT I) is an enzyme to transport a higher fatty acid from cytoplasm to a mitochondrial lo substrate, and plays an vital role in limiting the beta-oxidation rate.

Therefore, CPT I inhibitors will be utilized as an effective antidiabetic agent in that they may inhibit the beta-oxidation of higher fatty acids, increase the availability of glucose and exert the hypoglycemic, hypolipidemic and hypoketonemic effects.

The typical compounds belonging to the above mentioned CPT I inhibitors include palmoxirate, clomoxir(POCA) and etomoxir, and these compounds are characterized in that all of them have oxirane carboxylic acid in their most active site.

The inhibitory action of these oxirane carboxylic acid derivatives against the CPT I has yet to be elucidated up to now but it has been assumed that since these derivatives have the stable covalent bonding in the active sites of CPT I within cytoplasm, their inhibition action against the CPT I may contributed to the treatment of diabetes. Therefore, a possible mode of action is that when some nucleophilic substance at the active site of CPT I initiates to attack the epoxide ring structure of oxirane carboxylic acid derivatives, the opened epoxide ring forms a new hydroxyl group and at the same time, CPT I and oxirane carboxylic acid derivative is covalently bonded, thus inhibiting the CPT I activity.

However, the phase II clinical trials of etomoxir had been discontinued owing to some side effects associated with prolonged administration, such as enlarged heart and toxicity in the liver, but its cause has not been explicitly known up to now.

DISCLOSURE OF INVENTION

Based on the mechanism that these oxirane carboxylic acid derivatives have exerted inhibitory actions against the CPT I, the inventor et al. have extensively studied to develop some promising compounds with blood glucose lowering effects, thus showing remarkable antidiabetic activities and less side effects. To this end, the inventor et al. have come to know that as a result of screening various kinds of derivatives having oxirane carboxylic acid positioned at their most active sites, 2-hydroxypropionic acid derivative of the formula 1 with opened epoxy ring at oxirane structure has proven to have an excellent antidiabetic activity and less side effects. In consequence, this invention has been completed.

An object of this invention is to provide 2-hydroxypropionic acid derivative expressed by the following formula 1.

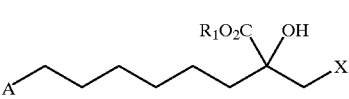

Wherein:

A is one selected from the radicals expressed by the following (i), (ii), (iii), (iv) and (v);

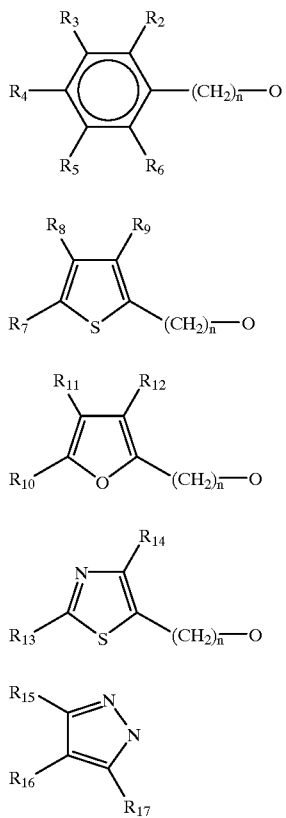

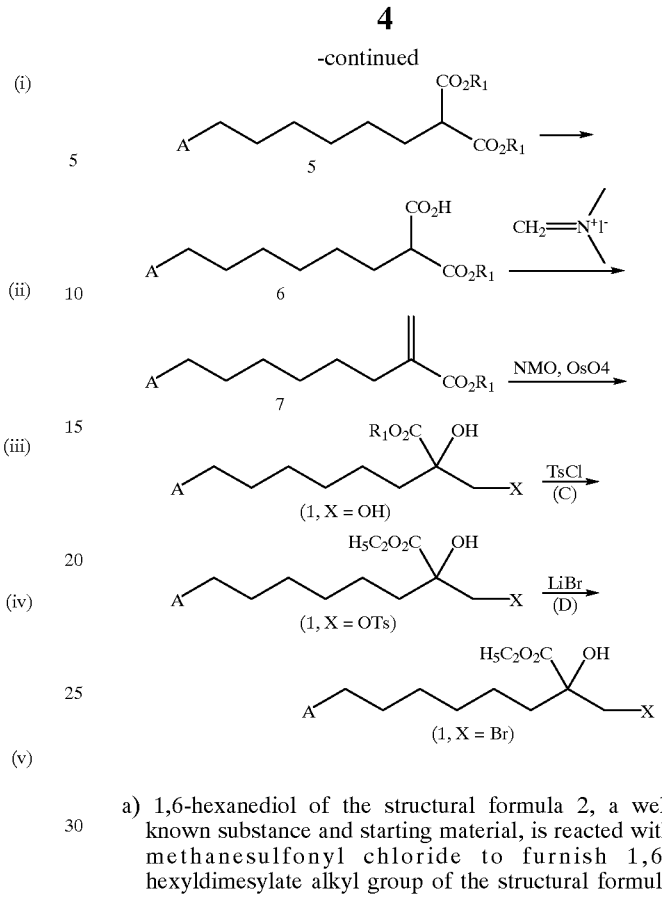

$R_1$ represents a lower alkyl;

X represents hydroxy, mesylate, tosylate or bromine. (wherein; $R_2$~$R_{17}$ represent independently hydrogen, halogen, alkoxy, lower alkyl, hydroxy, alkenyl, alkynyl, cyano or amino group; in particular, $R_2$, $R_3$, and $R_5$ are hydrogen; $R_4$ is hydrogen, chlorine or methoxy group; $R_7$, $R_8$ and $R_9$ are hydrogen or chlorine; $R_{10}$, $R_{14}$, $R_{15}$ and $R_{17}$ are hydrogen or methyl group; $R_{11}$, $R_{12}$, $R_{13}$ and $R_{16}$ are preferably hydrogen; n denotes 0, 1 or 2).

Another object of this invention is to provide some compounds expressed by the above mentioned formula 1.

Another object of this invention is also to provide an antidiabetic agent containing some compounds expressed by the above mentioned formula 1.

The compound of the formula 1 according to this invention may be prepared by the following reaction scheme 1:

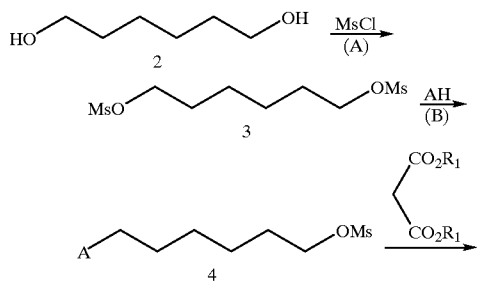

a) 1,6-hexanediol of the structural formula 2, a well known substance and starting material, is reacted with methanesulfonyl chloride to furnish 1,6-hexyldimesylate alkyl group of the structural formula 3, being mesylated to both alcohol groups;

b) 1,6-hexyldimesylate alkyl group is reacted with various kinds of aromatic alcohol derivatives in the presence of sodium hydride to synthesize the compound of the general formula 4 having an ether linkage and then, the compound, so synthesized, is further reacted with diethylmalonic acid to furnish the compound of the general formula 5;

c) The compound of the general formula 5 is hydrolyzed using potassium hydride to give the compound of the general formula 6 and then, Eschenmorser's salt is added to the compound of the general formula 6 to synthesize the compounds of the general formula 7, alpha, beta-unsaturated ester;

d) The compounds of the general formula 7, so synthesized, are dihydroxylated using osmium tetroxide as a catalyst to give a desired compound 1 (X=hydroxy), and under further tosylation and bromination, each desired of compound I having X=tosylate and X=bromine, respectively, may be obtained.

From the above reaction processes (A) and (B), 6-bromo-1-hexaneol and 1,6-dibromohexane may be replaced by 1,6-hexanediol, a starting material. Further, tosylation or direct substitution may also be replaced by mesylation.

From the above reaction processes (C) and (D), mesylation may be replaced by tosylation, and the process of using tetrabromomethane, triphenylphosphine and dichloromethane may gain the same results.

The compound of the formula 1 according to this invention may be used as an effective antidiabetic agent. The daily effective dose in adult is 10–100 mg/kg.

The compound of the formula 1 according to this invention has proven to have remarkable blood glucose lowering effects, while being safe in $LD_{50}$.

According to this invention, an antidiabetic agent containing the compound of the formula 1 as an active ingredient may be administered via the following common dosage forms, i.e., tablets, injections, capsules, etc.

This invention relates to a novel 2-hydroxypropionic acid derivative and its manufacturing method. Based on its inhibitory mechanism on the CPT I, 2-hydroxypropionic acid derivative of this invention has blood glucose lowering effects so that the above derivative may be effectively used as an antidiabetic agent having remarkable antidiabetic activity and less side effects.

BEST MODE FOR CARRYING OUT THE INVENTION

This invention is explained in more detail by the following examples, but the claims are not limited to these examples.

EXAMPLE 1

Ethyl-2,3-dihydroxy-2-(6-benzoxy)hexylpropionate

1) In a 500 ml round-bottomed flask, 60% sodium hydride (6.84 g, 170.92 mmol) was placed, and the air inside the flask was substituted by argon gas. Dry tetrahydrofuran (200 ml) was added dropwise thereto to form a suspension. After chilling the mixture to 0° C., a solution of 1,6-hexanediol (20 g, 169.23 mmol) in dry tetrahydrofuran (200 ml) was slowly added dropwise, and the mixture stirred at room temperature for 20 minutes. To the solution, benzylbromide (20.25 ml, 170.25 mmol) was added dropwise and stirred at room temperature for 18 hours. The reaction mixture was concentrated under reduced pressure to remove tetrahydrofuran as a solvent, and the residue was diluted with a mixture of ethyl acetate (400 ml) and water (50 ml). After washing with water (500 ml×2) and saturated brine (500 ml×2), the solution was dried over anhydrous magnesium sulfate, filtered and concentrated under reduced pressure. The residue was purified on a column chromatography (eluent: ethyl acetate/n-hexane=1/3) to give 19.47 g of object compound as colorless oil (yield: 55%).

IR(neat) 3400(alcohol) cm$^{-1}$ Mass(EI) 208(M$^+$-1) $^1$H NMR(80 MHz,CDCl$_3$) δ7.43 (s, 5H), 4.53 (s,2H), 3.66 (t, 2H), 3.50 (t, 2H), 1.81–1.20 (m, 8H)

2) In a 250 ml round-bottomed flask, 6-benzyloxy-1-hexanol (14.2 g, 67.87 mmol) and p-toluenesulfonyl chloride (14.23 g, 74.66 mmol) were placed, and the air inside the flask was substituted by argon gas. Dry chloroform (120 ml) was added dropwise thereto, and then dry pyridine (16.47 ml) was injected to the mixture. After stirring at room temperature for 3 hours, the reaction mixture was concentrated under reduced pressure to remove chloroform, and the residue was diluted with ethyl acetate (400 ml). The solution was washed with diluted aqueous hydrochloric acid (20 ml×2), water (30 ml×2) and saturated brine (30 ml×2), dried over anhydrous magnesium sulfate and filtered. After concentrating the solution under reduced pressure, the residue was purified on a column chromatography (eluent: ethyl acetate/n-hexane=1/10) to obtain 24 g of the object compound as colorless oil (yield: 97%).

Mass(EI) 362 (M$^+$-1) $^1$H NMR(400 MHz, CDCl$_3$) δ7.63 (d,2H), 7.15(s,7H), 4.33(s,2H), 3.86(t,2H), 3.27(t,2H), 2.29 (s,3H), 1.52–1.11(m,8H)

3) In a 250 ml three-necked round-bottomed flask, 60% sodium hydride (2.28 g, 56.94 mmol) was placed, and the air inside the flask was substituted by argon gas. Dry tetrahydrofuran (10 ml) was injected thereto to form a suspension. After chilling the mixture to 0° C., a solution of diethyl malonate (8.72 g, 54.46 mmol) in dry tetrahydrofuran (100 ml) was slowly added dropwise, and the mixture stirred for about 10 minutes. To the mixture, a solution of 6-benzoxy-1-(4-methylbenzenesulfoxy)hexane (17.99 g, 49.51 mmol) in dry tetrahydrofuran (200 ml) was injected. The reaction mixture was heated under reflux for 20 hours to complete the reaction. After removing tetrahydrofuran by evaporating under reduced pressure, the residue was diluted with a mixture of ethyl acetate (500 ml) and water (50 ml). After washing with water (50 ml×2) and saturated brine (50 ml×2), the solution was dried over anhydrous magnesium sulfate, filtered and concentrated under reduced pressure. The residue was purified on a column chromatography (eluent: ethyl acetate/n-hexane=1/20) to give 16 g of object compound as colorless oil (yield: 92%).

IR(neat) 1740(ester carbonyl) cm$^{-1}$ Mass(EI) 350(M$^+$-1) $^1$HNMR(400 MHz,CDCl$_3$) δ7.32(s,5H), 4.33(s,2H), 4.13(q, 4H), 3.84(t,2H), 3.25(t,1H), 1.11–1.70(m,16H)

4) In a 250 ml round-bottomed flask, diethyl 6-benzoxyhexyl malonate (15.9 g, 45.25 mmol) and 85% potassium hydroxide (3.2 g, 48.42 mmol) were placed, and ethanol (160 ml) was injected thereto. The mixture was stirred at room temperature for 24 hours. After concentrating the reaction mixture under reduced pressure to remove ethanol, the residue was diluted with 70 ml of water. The solution was washed with diethyl ether, and the aqueous layer was acidified with dilute aqueous hydrochloric acid, and then extracted by using ethyl acetate (400 ml). The organic layer was washed with water (50 ml×2) and saturated brine (50 ml×2), and dried over anhydrous magnesium sulfate. After filtering and concentrating under reduced pressure, crude product (14.6 g) was obtained as colorless oil (yield: 100%).

IR(cm$^{-1}$) 1740(ester, carbonyl of carboxylic acid), 3400 (OH of carboxylic acid) Mass(EI) 323(M$^+$) $^1$HNMR(400 MHz,CDCl$_3$) δ7.32(s,5H), 4.21(q,2H), 3.35(t,1H), 1.26(t, 3H), 4.5(s,2H), 3.45(t,2H), 1.90–1.31 (m,10H)

5) In a 50 ml round-bottomed flask, 60% sodium hydroxide (888.72 mg, 22.22 mmol) was placed, and the air inside the flask was substituted by argon gas. Dry tetrahydrofuran (10 ml) was added thereto to form a suspension. After chilling the suspension to 0° C., a solution of ethyl 6-benzoxyhexylmalonate (3.42 g, 10.58 mmol) in dry tetrahydrofuran (10 ml) was slowly added dropwise, and the mixture stirred at room temperature for 20 minutes. Eschenmoser salt (2.15 g) was added thereto at a time, and the resultant mixture was heated under reflux for 6 hours. After removing tetrahydrofuran by evaporating under reduced pressure, the residue was diluted with a mixture of ethyl acetate (100 ml) and water (20 ml). The solution was washed with 7% aqueous hydrochloric acid (10 ml×2), water (10 ml×2), saturated aqueous sodium bicarbonate solution (10 ml×2), water (10 ml×2) and saturated brine (10 ml×2), and dried over anhydrous magnesium sulfate. After filtering and concentrating the solution under reduced pressure, the residue was purified on a column chromatography (eluent: ethyl acetate/n-hexane=1/15) to give 2.5 g of the object compound as colorless oil (yield: 81%)

IR(cm$^{-1}$) 1740(ester carbonyl) Mass(EI) 291 (M$^+$) $^1$HNMR(500 MHz,CDCl$_3$) δ7.32(s,5H), 4.49(s,2H), 3.46(t, 2H), 1.63–1.33(m,8H), 6.11(s,1H), 4.20(q,2H), 2.27(t,2H), 1.29(t,3H), 5.4 8(s,1H)

6) In a 50 ml round-bottomed flask, 60% aqueous NMO solution 1.31 ml(7.55 mmol), and a mixed solution of acetone and water (50 ml, acetone/water=10/1) were placed, and 0.08 M solution of osmium tetroxide in toluene (4.28 ml, 0.343 mmol) was injected there to. The reaction mixture was added to ethyl 2-(6-benzoxy)hexyl-2-enepropionate (2 g, 6.86 mmol), and the resultant mixture was stirred at room temperature for 2 h ours. After adding sodium bisulfite, the reaction mixture was stirred for 20 minutes, and extracted with methylene chloride (100 ml). The solution was washed with saturated brine (10 ml×2), dried over anhydrous magnesium sulfate, filtered and concentrated under reduced pressure. The residue was purified on a column chromatography (eluent: ethyl acetate/n-hexane=1/1) to give 2.2 g of the object compound as white solid (yield: 98%).

IR (cm.$^{-1}$) 1740 (esteric carbonyl), 3450 (alcohol) Mass (EI) 325(M$^+$) $^1$HNMR(400 MHz,CDCl$_3$) δ7.26–7.34(m, 5H), 3.78(d,1H), 1.30(t,3H), 4.49(s,2H), 3.58(d,1H), 4.23–4.28(m,2H), 1.34–1.65(m,10H)

7) In a 25 ml round-bottomed flask, ethyl 2,3-dihydroxy-2-(6-benzoxy)hexylpropionate (230 mg,, 0.707 mmol) and p-toluenesulfonyl chloride (161.7 mg, 0.848 mmol) were placed, and the air inside the flask was substituted by argon gas. Dry chloroform (3 ml) was added dropwise thereto, and then dry pyridine (0.18 ml) was injected to the mixture. After stirring at room temperature for 18 hours, the reaction mixture was concentrated under reduced pressure to remove chloroform, and the residue was diluted with ethyl acetate (50 ml). The solution was washed with diluted aqueous hydrochloric acid (5 ml×2), water (50 ml×2) and saturated brine (50 ml×2), dried over anhydrous magnesium sulfate and filtered. After concentrating the solution under reduced pressure, the residue was purified on a column chromatography (eluent: ethyl acetate/n-hexane=1/5) to obtain 289 mg of the object compound as colorless oil (yield: 85%).

IR (cm.$^{-1}$) 1740 (esteric carbonyl) Mass(EI) 479(M$^+$) $^1$HNMR(400 Hz, CDCl$_3$) δ7.76(d,2H), 7.33(s,7H), 4.47(s, 2H), 4.23–4.20(m,2H), 4.22(d,1H) 3.88(d, 1H), 3.42(t,2H), 2.44(s,3H), 1.61–1.31 (m,10H), 1.28(t,3H)

EXAMPLE 2

Ethyl-2,3-dihydroxy-2-[6-(4-methoxybenzoxy) hexyl]propionate

The procedures described in Example 1-1)~1-6) were repeated but using 4-methoxybenzyl alcohol instead of benzyl alcohol of Example 1-1) to obtain the title compound.

IR(neat) 1740(ester carbonyl), 3450(alcohol)cm$^{-1}$ MASS (EI) 354(M$^+$-1) $^1$H NMR(80 MHz, CDCl$_3$) δ7.28(d, 2H), 6.90(d, 2H), 4.42(s, 2H), 4.27(q, 2H), 3.81(s, 3H), 1.91–1.07 (m, 10H), 1.31(t, 3H)

EXAMPLE 3

Ethyl-2,3-dihydroxy-2-[6-(4-chlorophenoxy)hexyl] propionate

The procedures described in Example 1-1)~1-6) were repeated but using 4-chlorophenol instead of benzyl alcohol of Example 1-1) to obtain the title compound.

IR(neat) 1740(ester carbonyl), 3400(alcohol)cm$^{-1}$ MASS (EI) 344(M$^+$-1) $^1$H NMR(400 MHz, CDCl$_3$) δ7.22(d, 2H), 6.81(d, 2H), 4.25–4.17(m, 2H), 3.90(t, 2H), 3.03(d, 1H), 2.78(d, 1H), 1.78–1.38(m, 10H), 1.27(t, 3H)

EXAMPLE 4

Ethyl-2,3-dihydroxy-2-[6-(3,5-dimethylpyrazol)hexyl] propionate

The procedures described in Example 1-1)~1-6) were repeated but using 3,5-dimethylpyrazol-1-methanol instead of benzyl alcohol of Example 1-1) to obtain the title compound.

IR(neat) 1740(ester carbonyl), 3400(alcohol) MASS(EI) 314(M$^+$) $^1$H NMR(80 MHZ) δ5.73(s,1H) 4.25(q,2H), 3.89 (t,2H) 3.61(m,2H) 2.18(s,6H) 1.80–1.19(m,10H)

EXAMPLE 5

Ethyl-2,3-dihydroxy-2-[6-(5-methyl-2-furanmethoxy) hexyl]propionate

The procedures described in Example 1-1)~1-6) were repeated but using 5-methyl-2-furan-methanol instead of benzyl alcohol of Example 1-1) to obtain the title compound.

$^1$H NMR (300 MHz, CDCl$_3$) δ6.17(d, 1H), 5.91(d, 1H), 4.36(s, 2H), 3.78(t, 1H), 3.59(d, 1H), 3.53(s, 1H), 3.44(t, 2H), 2.29(s, 3H), 2.1(m, 1H), 1.7–1.0(m, 10H), 1.31(t, 3H)

EXAMPLE 6

Ethyl-2,3-dihydroxy-2-[6-(2-thiophenethoxy)hexyl] propionate

The procedures described in Example 1-1)~1-6) were repeated but using 2-thiopenethanol instead of benzyl alcohol of Example 1-1) to obtain the title compound.

$^1$H NMR (300 MHz, CDCl$_3$) δ7.14(dd, 1H), 6.93(dd, 1H), 6.85(dd, 1H), 4.31(dq—dq, 2H), 3.79(t, 1H), 3.7–3.5(m, 4H), 3.44(t, 2H), 3.09(t, 2H), 2.10(m, 1H), 1.7–1.0(m, 9H), 1.32(t, 3H)

EXAMPLE 7

Ethyl-2,3-dihydroxy-2-[6-(5-chloro-2-thiophenmethoxy) hexyl]propionate

The procedures described in Example 1-1)~1-6) were repeated but using 5-chloro-2-thiophenmethanol instead of benzyl alcohol of Example 1-1) to obtain the title compound.

$^1$H NMR (300 MHz, CDCl$_3$) δ6.77(d, 1H), 6.74(d, 1H), 4.53(s, 2H), 4.28(dq—dq, 2H), 3.78(m, 1H), 3.59(d, 1H), 3.54(s, 1H), 3.44(t, 2H), 2.15(m, 1H), 1.7–1.0(m, 9H), 1.31(t, 3H)

EXAMPLE 8

Ethyl-2,3-dihydroxy-2-[6-(3-chloro-2-thiophenmethoxy) hexyl]propionate

The procedures described in Example 1-1)~1-6) were repeated but using, 3-chloro-2-thiophenmethoxy instead of benzyl alcohol of Example 1-1) to obtain the title compound.

$^1$H NMR (300 MHz, CDCl$_3$) δ7.26(d, 1H), 6.89(d, 1H), 4.63(s, 2H), 4.28(dq—dq, 2H), 3.78(t, 1H), 3.59(d, 1H), 3.53(s, 1H), 3.46(t, 2H), 2.1(m, 1H), 1.7–1.1(m, 9H), 1.31(t, 3H)

EXAMPLE 9

Ethyl 2-hydroxy-2-bromo-2-[6-(4-chlorophenoxy) hexyl]propionate

In a 25 ml round-bottomed flask, ethyl 2,3-dihydroxy-2-[6-(4-chlorophenoxy)hexyl] propionate (105 mg, 0.305 mmol) obtained from Example 3 was placed, and the air inside the flask was substituted by argon gas. Dry methylene chloride (1 ml) was injected thereto. To the mixture, a solution of triphenylphosphine (160 mg, 0.61 mmol) in dry methylene chloride (2 ml) and that of tetrabromomethane 101.2 mg (0.305 mmol) in dry methylene chloride (1.5 ml) were added sequentially. The resultant mixture was stirred at room temperature for 20 hours. After concentrating the reaction solution under reduced pressure, the residue was purified on a column chromatography (eluent: ethyl acetate/n-hexane=1/1) to give 110 mg of the object compound as white solid (yield: 89%).

$^1$HNMR(400 MHz, CDCl$_3$) δ7.72(d,2H), 6.80(d,2H), 4.29(q,2H), 3.89(t,2H), 3.77(d,1H) 3.58(d,1H), 1.76–1.33 (m,10H), 1.28(t,3H)

EXAMPLE 10

Ethyl 2-hydroxy-3-(4-methylbenzenesulfoxy)-2-[6-benzoxyhexyl]propionate

In a 25 ml round-bottomed flask, ethyl 2,3-dihydroxy-2-[6-(benzoxy)hexyl]propionate (230 mg, 0.707 mmol) prepared from Example 1 and p-toluenesulfonyl chloride (161.7 mg, 0.848 mmol) were placed, and the air inside the flask was substituted by argon gas. Dry chloroform (3 ml) was added dropwise thereto, and then dry pyridine (0.18 ml) was injected to the mixture. After stirring at room temperature for 18 hours, the reaction mixture was concentrated under reduced pressure to remove chloroform, and the residue was diluted with ethyl acetate (50 ml). The solution was washed with diluted aqueous hydrochloric acid (5 ml×2), water (50 ml×2) and saturated brine (50 ml×2), dried over anhydrous magnesium sulfate and filtered. After concentrating the solution under reduced pressure, the residue was purified on a column chromatography (eluent: ethyl acetate/n-hexane=1/5) to obtain 289 mg of the object compound as colorless oil (yield: 85%).

IR(cm$^{-1}$) 1740(ester carbonyl) Mass(EI) 479(M$^+$) $^1$HNMR(400 MHz,CDCl$_3$) δ7.76(d,2H), 7.33(s,7H), 4.47(s, 2H), 4.23–4.20(m,2H), 4.22(d,1H), 3.88 (d, 1H), 3.42(t,2H), 2.44(s,3H), 1.61–1.31 (m, 10H), 1.28(t,3H)

EXAMPLE 11

Ethyl 2-hydroxy-3-bromo-2-[6-(2-thiophenethoxy) hexyl]propionate

1) Ethyl-2,3-dihydroxy-2-[6-(2-thiophenethoxy)hexyl] propionate (580 mg, 1.7 mmol) prepared from Example 6 was dissolved in dry pyridine 10 ml, and p-toluenesulfonyl chloride (3.31 g, 17 mmol) was added thereto. The mixture was stirred at room temperature for 3 hours. The reaction mixture was diluted by adding ethyl acetate (50 ml), and the resultant solution was washed with 1N diluted aqueous hydrochloric acid, 5% aqueous sodium bicarbonate solution (40 ml×2), distilled water (40 ml) and saturated brine (20 ml). The solution was dried over anhydrous magnesium sulfate, filtered and concentrated under reduced pressure. The residue was purified on a column chromatography (eluent: ethyl acetate/n-hexane=1/10) to give 770 mg of ethyl 2-hydroxy-3-(4-methylbenzenesulfoxy)-2-[6-(2-thiophenmethoxy)hexyl]propionate as pale yellow oil (yield: 88.9%).

$^1$H NMR (300 MHz, CDCl$_3$) δ7.77 (2H, d, J=8.09 Hz, benzene H), 7.34 (2H, d, J=7.95 Hz, benzene H), 7.13 (1H, d, thiophene H$_5$), 6.92 (1H, m, thiophene H$_4$), 6.84 (1H, s(br), thiophene H$_3$), 4.22 (3H, m, CO$_2$CH$_2$C$_3$, 1H of —CH$_2$—OTs), 3.99 (1H, d, J=9.68 Hz, 1H of —CH$_2$—OTs), 3.63 (2H, t, J=6.73 Hz, Ar—CH$_2$CH$_2$O—), 3.42 (2H, t, J=6.41 Hz, ArCH$_2$CH$_2$O—CH$_2$—), 3.36 (1H, s, t-OH), 3.08 (2H, t, J=6.62 Hz, Ar—CH$_2$CH$_2$O—), 2.45 (3H, s, tosyl-CH$_3$), 1.54 (5H, m, aliphatic H), 1.27 (3H, t, CO$_2$CH$_2$CH$_3$, 4H, m, aliphatic H), 1.08 (1H, m, aliphatic H)

2) Dissolved was ethyl 2-hydroxy-3-(4-methylbenzenesulfoxy)-2-[6-(2-thiophenmethoxy) hexyl] propionate (203 mg, 0.4 mmol) in acetone (7 ml), and lithium bromide (0.36 g, 4.2 mmol) was added thereto. After heating under reflux for 16 hours, the reaction mixture was concentrated under reduced pressure to remove acetone. The residue was diluted with ethyl acetate (20 ml), and the organic layer was washed with distilled water (20 ml) and saturated brine (10 ml), dried over anhydrous magnesium sulfate, filtered and concentrated under reduced pressure. The residue was purified on a column chromatography (eluent: ethyl acetate/n-hexane=1/5) to give 160 mg of object compound as colorless oil (yield: 96.9%)

$^1$H NMR (300 MHz, CDCl$_3$) δ7.14 (1H, dd, J=5.16 Hz, J=1.07 Hz, thiophene H.), 6.93 (1H, dd, J=5.03 Hz, J=3.46 Hz, thiophene H$_4$), 6.84 (1H, m, thiophene H$_3$), 4.29 (2H, m, CO$_2$CH$_2$CH$_3$), 3.67 (1H, d, J=10.28 Hz, 1H of —CH$_2$—Br), 3.64 (2H, t, J=6.82 Hz, Ar—CH$_2$CH$_2$O—), 3.51 (1H, s, t-OH), 3.47 (1H, d, J=10.18 Hz, 1H of —CH$_2$—Br), 3.44 (2H, t, J=6.56 Hz, ArCH$_2$CH$_2$O—CH$_2$—), 3.09 (2H, t, J=6.80 Hz, Ar—CH$_2$CH$_2$O—), 1.85~1.45 (4H, m, aliphatic H), 1.4~1.2 (5H, m, aliphatic H, 3H, t, CO$_2$CH$_2$CH$_3$), 1.15 (1H, m, aliphatic H) $^{13}$C NMR (75 MHz, CDCl$_3$) δ173.51, 141.38, 126.59, 125.0, 123.56, 77.0, 71.35, 70.90, 62.50, 39.72, 37.30, 30.45, 29.50, 29.32, 25.88, 23.79, 14.24

EXAMPLE 12

Ethyl 2-hydroxy-3-bromo-2-[6-(5-chlorothiophenemethoxy)hexyl]propionate

The object compound was prepared by the same procedures as Example 11 but using ethyl 2,3-dihydroxy-2-[6-(5-chlorothiophenemethoxy)hexyl]propionate instead of ethyl 2,3-dihydroxy-2-[6-(2-thiophenethoxy)hexyl]propionate.

$^1$H NMR (300 MHz, CDCl$_3$) δ6.77(d, 1H), 6.74(d, 1H), 4.53(s, 2H), 4.29(dq—dq, 2H), 3.66(d, 1H), 3.51(s, 1H), 3.47(d, 1H), 3.44(t, 2H), 1.85–1.1(m, 10H), 1.33(t, 3H)

$^{13}$C NMR (75 MHz, CDCl$_3$) δ
173.48, 140.45, 129.91, 125.52, 125.27, 70.0, 67.54, 62.48, 39.69,37.28, 29.42, 29.27, 25.80, 25.82, 23.76, 14.23

EXAMPLE 13

Ethyl 2-hydroxy-3-bromo-2-[6-(3-chlorothiophenemethoxy)hexyl]propionate

The object compound was prepared by the same procedures as Example 11 but using ethyl 2,3-dihydroxy-2-[6-(3-chlorothiophenemethoxy)hexyl]propionate instead of ethyl 2,3-dihydroxy-2-[6-(2-thiophenethoxy) hexyl]propionate.

$^1$H NMR (300 MHz, CDCl$_3$) δ7.26(d, 1H), 6.89(d, 1H), 4.63(s, 2H), 4.29(dq—dq, 2H), 3.66(d, 1H), 3.50(s, 1H), 3.48(t, 2H), 3.47(d, 1H), 1.85–1.1(m, 10H), 1.32(t, 3H)

$^{13}$C NMR (75 MHz, CDCl$_3$) δ
173.49, 134.05, 127.47,124.68,123.45, 70.28, 64.79, 62.48, 39.69, 37.29, 29.40, 29.26, 25.7, 25.79, 23.76, 14.23

EXAMPLE 14

Ethyl-2,3-dihydroxy-2-[6-(5-methyl-2-thiophenmethoxy) hexyl]propionate

The procedures described in Example 1-1)~1-6) were repeated but using 5-methyl-2-thiophenmethanol instead of benzyl alcohol of Example 1-1) to obtain the title compound.

$^1$H NMR (300 MHz, CDCl$_3$) δ6.76 (1H, d, J=3.36 Hz, thiophene H$_3$), 6.60 (1H, m, thiophene H$_4$), 4.55 (2H, s, Ar—CH$_2$O—), 4.28 (2H, m, CO$_2$CH$_2$—CH$_3$), 3.78 (1H, t(br), 1H of —CH$_2$—OH), 3.59 (1H, dd, 1H of —CH$_2$—

OH), 3.54 (1H, s, t-OH), 3.43 (2H, t, J=6.52 Hz, ArCH$_2$O—CH$_2$—), 2.46 (3H, sd, J=0.88 Hz, thiophene-CH$_3$), 2.14 (1H, dd, —CH$_2$—OH), 1.58 (4H, m, aliphatic H), 1.31 (5H, m, aliphatic H), 1.31 (3H, t, J=7.15 Hz, CO$_2$CH$_2$CH$_3$), 1.1 (1H, m, aliphatic H)

EXAMPLE 15

Ethyl-2,3-dihydroxy-2-[6-(5-methoxy-2-thiophenmethoxy)hexyl]propionate

The procedures described in Example 1-1)~1-6) were repeated but using 5-methoxy-2-thiophenmethoxy instead of benzyl alcohol of Example 1-1) to obtain the title compound.

$^1$H NMR (300 MHz, CDCl$_3$) δ6.59 (1H, d, J=3.76 Hz, thiophene H$_3$), 6.03 (1H, d, J=3.78 Hz, thiophene H$_4$), 4.48 (2H, s, Ar—CH$_2$O—), 4.28 (2H, m, J=7.15 Hz, CO$_2$CH$_2$CH$_3$), 3.87 (3H, s, —OCH$_3$), 3.78 (1H, t, 1H of —CH$_2$—OH), 3.59 (1H, dd, 1H of —CH$_2$—OH), 3.52 (1H, s, t-OH), 3.42 (2H, t, J=6.53 Hz, ArCH$_2$O—CH$_2$—), 2.1 (1H, dd, —CH$_2$—OH), 1.67 1.31 (9H, m, aliphatic H), 1.31 (3H, t, J=7.12 Hz, CO$_2$CH$_2$CH$_3$), 1.1 (1H, m, aliphatic H)

EXAMPLE 16

Ethyl-2,3-dihydroxy-2-[6-(4-methoxy-2-thiophenmethoxy)hexyl]propionate

The procedures described in Example 1-1)~1-6) were repeated but using 4-methoxy-2-thiophenmethanol instead of benzyl alcohol of Example 1-1) to obtain the title compound.

$^1$H NMR (300 MHz, CDCl$_3$) δ6.65 (1H, s, thiophene H), 6.18 (1H, d, J=1.27 Hz, thiophene H), 4.54 (2H, s, Ar—CH$_{2O}$—), 4.28 (2H, q(br), CO$_2$CH$_2$CH$_3$), 3.78 (3H, s, —OCH$_3$), 3.60 (s, t-OH), 3.55 (1H, d, J=8.96 Hz, 1H of —CH$_2$—OH), 3.45 (3H, t, J=6.49 Hz, ArCH$_2$O—CH$_2$—, 1H of —CH$_2$—OH), 2.15 (1H, br, —CH$_2$—OH), 1.65~1.1 (10H, m, aliphatic H), 1.31 (3H, t, CO$_2$CH$_2$CH$_3$)

EXAMPLE 17

Ethyl-2,3-dihydroxy-2-[6-(3-thiophenmethoxy) hexyl]propionate

The procedures described in Example 1-1)~1-6) were repeated but using 3-thiophenmethanol instead of benzyl alcohol of Example 1-1) to obtain the title compound. $^1$H NMR (300 MHz, CDCl$_3$) δ7.29 (1H, m, thiophene H$_5$), 7.20 (1H, s(br), thiophene H$_2$), 7.07 (1H, d(br), J=4.77 Hz, thiophene H$_4$), 4.50 (2H, s, Ar—CH$_2$O—), 4.28 (2H, q, J=7.11 Hz, CO$_2$CH$_2$CH$_3$), 3.78 (1H, t, 1H of —CH$_2$—OH), 3.59 (1H, d, J=11.20 Hz, 1H of —CH$_2$—OH), 3.54 (1H, t-OH), 3.44 (2H, t, J=6.50 Hz, ArCH$_2$O—CH$_2$—), 2.16 (1H, br, —CH$_2$—OH), 1.6 (5H, m, aliphatic H), 1.3 (4H, m, aliphatic H), 1.3 (3H, t, J=7.10 Hz, CO$_2$CH$_2$CH$_3$)

EXAMPLE 18

Ethyl-2,3-dihydroxy-2-[6-(3-thiophenethoxy)hexyl] propionate

The procedures described in Example 1-1)~1-6) were repeated but using 3-thiophenethanol instead of benzyl alcohol of Example 1-1) to obtain the title compound.

$^1$H NMR (300 MHz, CDCl$_3$) δ7.25 (1H, dd, J=4.93 Hz, J=3.03 Hz, thiophene H$_5$), 7.02 (1H, m, thiophene H$_2$), 6.98 (1H, dd, J=4.9 Hz, J=1.13 Hz, thiophene H$_4$), 4.28 (2H, m, CO$_2$CH$_2$CH,), 3.77 (1H, m, 1H of —CH$_2$—OH), 3.62 (2H, t, J=7.03 Hz, Ar—CH$_2$CH$_2$O—), 3.59 (1H, d, J=11.21 Hz, 1H of —CH$_2$—OH), 3.55 (1H, s, t-OH), 3.42 (2H, t, J=6.58 Hz, ArCH$_2$CH$_2$O—CH$_2$—), 2.91 (2H, t, J=7.0 Hz, Ar—CH$_2$CH$_2$O—), 2.1 (1H, m, —CH$_2$—OH), 1.72~1.23 (9H, m, aliphatic H), 1.32 (3H, t, J=7.09 Hz, CO$_2$CH$_2$CH$_3$), 1.09 (1H, m, aliphatic H)

EXAMPLE 19

Ethyl-2,3-dihydroxy-2-[6-(2-thiophenoxy)hexyl] propionate

The procedures described in Example 1-1)~1-6) were repeated but using 2(5H)-thiophenone instead of benzyl alcohol of Example 1-1) to obtain the title compound.

$^1$H NMR (300 MHz, CDCl$_3$) δ6.71 (1H, dd, J=3.76 Hz, J=5.82 Hz, thiophene H$_4$), 6.54 (1H, dd, J=5.75 Hz, J=1.43 Hz, thiophene H$_5$), 6.19 (1H, dd, J=3.75 Hz, J=1.46 Hz, thiophene H$_3$), 4.29 (2H, dq—dq, J=7.15 Hz, CO$_2$CH$_2$CH$_3$), 4.01 (2H, t, J=6.42 Hz, ArO—CH$_2$—), 3.79 (1H, t(br), 1H of CH$_2$—OH), 3.59 (1H, dd, 1H of —CH$_2$—OH), 3.55 (1H, s, t-OH), 2.12 (1H, m, CH$_2$—OH), 1.80~1.25 (9H, m, aliphatic H), 1.32 (3H, t, J=7.13 Hz, CO$_2$CH$_2$—CH$_3$), 1.13 (1H, m, aliphatic H)

EXAMPLE 20

Ethyl-2,3-dihydroxy-2-[6-(2-thiophenmethoxy) hexyl]propionate

The procedures described in Example 1-1)~1-6) were repeated but using 2-thiophenmethanol instead of benzyl alcohol of Example 1-1) to obtain the title compound.

$^1$H NMR (300 MHz, CDCl$_3$) δ7.28 (1H, dd, J=4.65 Hz, J=1.74 Hz, thiophene H$_5$), 6.98~6.96 (2H, m, thiophene H$_3$, H$_4$), 4.65 (2H, s, Ar—CH$_2$O—), 4.27 (2H, dq—dq, CO$_2$CH$_2$CH$_3$, J=7.2 Hz, J$_{gem}$=14.2 Hz), 3.78 (1H, t, 1H of —CH$_2$—OH), 3.58 (1H, dd, J$_{gem}$=11.20 Hz, 1H of —CH$_2$—OH), 3.55 (1H, s, t-OH, D$_2$O exchangeable), 3.46 (2H, t, J=6.6 Hz, ArCH$_2$O—CH$_2$—), 2.19 (1H, dd, —CH$_2$—OH, D$_2$O exchangeable), 1.7~1.5 (5H, m, aliphatic H), 1.4–1.2 (4H, m, aliphatic H), 1.31 (3H, t, J=7.17 Hz, CO$_2$CH$_2$CH$_3$), 1.1 (1H, m, aliphatic H)

EXAMPLE 21

Ethyl 2-hydroxy-3-bromo-2-[6-(4-methoxy-2-thiophenemethoxy)hexyl]propionate

The object compound was prepared by the same procedures as Example 11 but using ethyl 2,3-dihydroxy-2-[6-(4-methoxy-2-thiophenemethoxy)hexyl]propionate instead of ethyl 2,3-dihydroxy-2-[6-(2-thiophenethoxy)hexyl] propionate.

$^1$H NMR (300 MHz, CDCl$_3$) δ6.65 (1H, s, thiophene H), 6.17 (1H, s, thiophene H), 4.53 (2H, s, Ar—CH$_2$O—), 4.29 (2H, m, CO$_2$CH$_2$CH$_3$), 3.78 (3H, s, —OCH$_3$), 3.66 (1H, d, J=10.24 Hz, 1H of —CH$_2$—Br), 3.53~3.42 (4H, m, 1H of —CH$_2$—Br, ArCH$_2$O—CH$_2$—, t-OH), 1.85~1.16 (13H, m, aliphatic H, CO$_2$CH$_2$CH$_3$) $^{13}$C NMR (75 MHz, CDCl$_3$) δ 173.45, 157.52, 140.49, 118.27, 96.44, 76.95, 69.95, 67.62, 62.44, 57.09, 39.67, 37.26, 29.41, 29.25, 25.78, 23.72, 14.20

EXAMPLE 22

Ethyl 2-hydroxy-3-bromo-2-[6-(3-thiophenemethoxy) hexyl]propionate

The object compound was prepared by the same procedures as Example 11 but using ethyl 2,3-dihydroxy-2-[6-(3- thiophenemethoxy)hexyl]propionate instead of ethyl 2,3-dihydroxy-2-[6-(2-thiophenethoxy)hexyl]propionate.

$^1$H NMR (300 MHz, CDCl$_3$) δ7.30 (1H, dd, J=4.82 Hz, J=3.0 Hz, thiophene H$_5$), 7.20 (1H, s(br), thiophene H$_2$), 7.07 ((H, d, J=4.82 Hz, thiophene H$_4$), 4.50 (2H, s, Ar—CH$_2$—), 4.29 (2H, m, CO$_2$CH$_2$CH$_3$), 3.67 (1H, d, J=10.25 Hz, 1H of —CH$_2$—Br), 3.51 (1H, d, J=9.4 Hz, 1H of —CH$_2$—Br), 3.44 (2H, t, J=6.53 Hz, ArCH$_2$O—C$_2$), 3.46 (1H, s, t-OH), 1.8~1.5 (5H, m, aliphatic H), 1.33 (3H, t, J=7.11 Hz, CO$_2$CH$_2$—CH$_3$), 1.33 (4H, m, aliphatic H), 1. 14 (1H, m, aliphatic H) $^{13}$C NMR (75 MHz, CDCl$_3$) δ173.48, 139.74, 127.26, 125.85, 122.50, 77.0, 70.17, 68.07, 62.47, 39.69, 37.29, 29.52, 29.32, 25.89, 23.78, 14.22

EXAMPLE 23

Ethyl 2-hydroxy-3-bromo-2-[6-(3-thiophenethoxy) hexyl]propionate

The object compound was prepared by the same procedures as Example 11 but using ethyl 2,3-dihydroxy-2-[6-(3-thiophenethoxy)hexyl]propionate instead of ethyl 2,3-dihydroxy-2-[6-(2-thiophenethoxy)hexyl]propionate.

$^1$H NMR (300 MHz, CDCl$_3$) δ7.25 (1H, dd, J=4.88 Hz, J=2.97 Hz, thiophene H$_5$), 7.02 (1H, m, thiophene H$_2$), 6.98 (1H, dd, J=4.89 Hz, J=1.17 Hz, thiophene H$_4$), 4.3 (2H, m, CO$_2$CH$_2$CH$_3$), 3.67 (1H, d, J=10.25 Hz, 1H of —CH$_2$—Br), 3.62 (2H, t, J=7.08 Hz, Ar—CH$_2$CH$_2$O—), 3.52 (1H, s, t-OH), 3.48 (1H, d, J=10.23 Hz, 1H of —CH$_2$—Br), 3.42 (2H, t, J=6.57 Hz, ArCH$_2$CH$_2$O—CH$_2$—), 2.94 (2H, t, J=7.01 Hz, Ar—CH$_2$CH$_2$O—), 1.85–1.1 (10H, m, aliphatic H), 1.33 (3H, t, J=7.1 Hz, CO$_2$CH$_2$CH$_3$)

EXAMPLE 24

Ethyl 2-hydroxy-3-bromo-2-[6-(2-thiophenemethoxy) hexyl]propionate

The object compound was prepared by the same procedures as Example 11 but using ethyl 2,3-dihydroxy-2-[6-(2-thiophenemethoxy)hexyl]propionate instead of ethyl 2,3-dihydroxy-2-[6-(2-thiophenethoxy)hexyl]propionate.

$^1$H NMR (300 MHz, CDCl$_3$) δ7.28 (1H, s(br), thiophene H$_5$), 6.96 (2H, m, thiophene H$_3$, H$_4$), 4.64 (2H, s, Ar—CH$_2$O—), 4.28 (2H, m, CO$_2$CH$_2$CH$_3$), 3.66 (1H, d, J=10.24 Hz, 1H of —CH$_2$—Br), 3.54 (1H, s(br), t-OH), 3.46 (1H, d, J=10.01 Hz, 1H of —CH$_2$—Br), 3.45(2H, t, J=6.36 Hz, ArCH$_2$O—CH$_2$—), 1.83~1.5 (5H, m, aliphatic H), 1.4~1.2 (4H, m, aliphatic H), 1.32 (3H, t, J=7.1 Hz, CO$_2$CH$_2$CH$_3$), 1.16 (1H, m, aliphatic H) $^{13}$C NMR (75 MHz, CDCl$_3$) δ

173.38, 141.34, 126.46, 126.01, 125.49, 76.89, 69.82, 67.19, 62.37, 39.64, 37.21, 29.37, 29.20, 25.75, 23.67, 14.15

EXPERIMENTAL EXAMPLE 1

Blood Glucose Lowering Effects of the Compounds Prepared by the Procedures of Example 1–13

Two groups of male diabetes-induced Sprague-Dawley rats (each of 4–5 rats weighing about 250 g per group) were used for this experiment. 45 mg/kg of streptozotocin (STZ) dissolved in 0.1M citrate buffer (pH 4.5, 0–4° C.) was injected to the tail vein of fasted rats for 1 day. After elapse of 7 days, their blood glucose concentration were measured and animals having the blood serum concentration of more than 350 mg/dl were used as diabetes-induced rats for this experiment. The rats were intravenously administered at a daily dose of 1 ml/kg, while the normal control group received equal volume of 0.1M citrate buffer.

7 days after being treated with streptozotocin, diabetes-induced rats were orally administered at a dose of 50 mg/kg of the compounds prepared by the procedures of Examples 1–13. Then, at time intervals of 90 mins, 120 mins and 180 mins, their blood glucose concentrations were measured and the smallest values were taken. The compounds of Example 1–13 were dissolved in 30% ethanol until its final concentration became 2 ml/kg, while the control group was orally received equal volume of 30% ethanol.

Significant difference between two groups was determined by ANOVA test, together with a post hoc test using Newman-Keuls test.

The test results was shown in the following table 1.

TABLE 1

| Blood glucose lowering effects of the Examples 1–13 | |
|---|---|
| Compound | Blood glucose lowering rate % |
| Example 1 | 38.5 |
| Example 2 | 10.0 |
| Example 3 | 23.0 |
| Example 4 | 19.8 |
| Example 5 | 22.0 |
| Example 6 | 1.2 |
| Example 7 | 19.2 |
| Example 8 | 26.0 |
| Example 9 | 22.0 |
| Example 10 | 34.1 |
| Example 11 | 13.0 |
| Example 12 | 26.4 |
| Example 13 | 19.3 |

As noted in the above table 1, the compounds of this invention have proven to have remarkable blood glucose lowering effects on diabetes-induced rats.

EXPERIMENTAL EXAMPLE 2

Toxicity test

The acute toxicity tests on rats were performed using the compound prepared by the procedure of the Example 1. Mature rats weighing 200–250 g were orally given the compound of the Example 1 dissolved in ethylacetate in parallel with its gradually increasing concentration. Then, LD$_{50}$ was calculated by number of killed animals. LD$_{50}$ was 481.5 mg/kg.

We claim:

1. A compound of the following formula 1 or a pharmaceutically acceptable salt thereof;

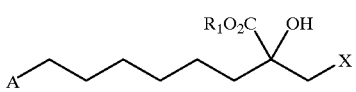

1

Wherein:

A is one selected from the radicals expressed by the following (i), (ii), (iii), (iv) and (v);

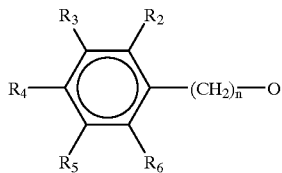
(i)

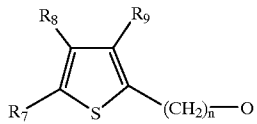
(ii)

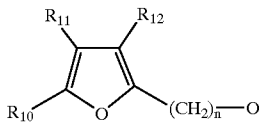
(iii)

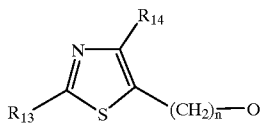
(iv)

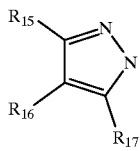
(v)

$R_1$ represents a lower alkyl;

X represents hydroxy, mesylate, tosylate or bromine.

(wherein $R_2$~$R_{17}$ represent independently hydrogen, halogen, alkoxy, lower alkyl, hydroxy, alkenyl, alkynyl, cyano or amino group; n denotes 0, 1 or 2).

2. A compound of the formula 1 or a pharmaceutically acceptable salt thereof according to claim 1, wherein:

A is one expressed by the following radical (i);

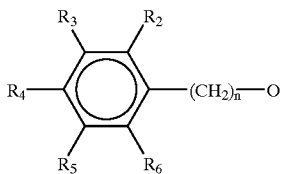
(i)

$R_2 R_3$ and $R_5$ are hydrogen;

$R_4$ is hydrogen, chlorine or methoxy group.

3. A compound of the formula I or a pharmaceutically acceptable salt thereof according to claim 1, wherein:

A is one expressed by the following radical (ii);

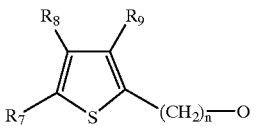
(ii)

$R_7$, $R_8$ and $R_9$ are hydrogen or chlorine.

4. A compound of the formula 1 or a pharmaceutically acceptable salt thereof according to claim 1, wherein:

A is one expressed by the following radical (iii);

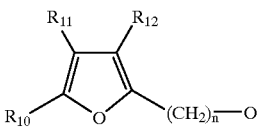
(iii)

$R_{10}$ is hydrogen or methyl group;

$R_{11}$ and $R_{12}$ are hydrogen.

5. A compound of the formula 1 or a pharmaceutically acceptable salt thereof according to claim 1, wherein:

A is one expressed by the following radical (iv);

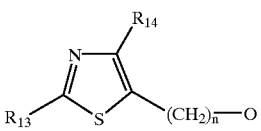
(iv)

$R_{13}$ is hydrogen;

$R_{14}$ is hydrogen or methyl group.

6. A compound of the formula I or a pharmaceutically acceptable salt thereof according to claim 1, wherein:

A is one expressed by the following radical (v);

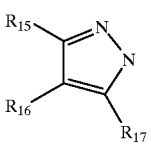
(v)

$R_{15}$ and $R_{17}$ are hydrogen or methyl group;

$R_{16}$ is hydrogen.

7. A process for manufacturing the Compound of the formula I according to claim 1, wherein:

a) 1,6-hexanediol of the structural formula 2, a well known substance and starting material, is reacted with methanesulfonyl chloride to furnish 1,6-hexyldimesylate alkyl group of the structural formula 3, being mesylated to both alcohol groups;

b) 1,6-hexyldimesylate alkyl group is reacted with various kinds of aromatic alcohol derivatives in the presence of sodium hydride to synthesize the compound of the general formula 4 having an ether linkage and then, the compound, so synthesized, is further reacted with diethylmalonic acid to furnish the compound of the general formula 5;

c) The compound of the general formula 5 is hydrolyzed using potassium hydride to give the compound of the general formula 6 and then, Eschenmorser's salt is added to the compound of the general formula 6 to synthesize the compounds of the general formula 7, alpha, beta-unsaturated ester;

d) The compounds of the general formula 7, so synthesized, are dihydroxylated using osmium tetroxide as a catalyst to give a desired compound 1 (X=hydroxy), and under further tosylation and bromination, each desired of compound I having X=tosylate and X=bromine, respectively, may be obtained.

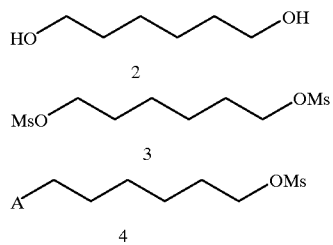

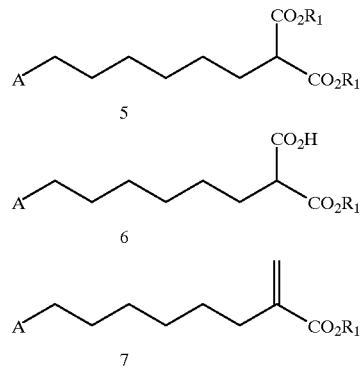

8. An antidiabetic agent containing the compound or a pharmaceutically acceptable salt thereof expressed by the formula 1 according to claim 1.

* * * * *